(12) United States Patent
Minamoto et al.

(10) Patent No.: US 7,963,985 B2
(45) Date of Patent: Jun. 21, 2011

(54) INSTRUMENT FOR ULTRAVIOLET IRRADIATION AND ULTRAVIOLET IRRADIATING APPARATUS

(75) Inventors: Maki Minamoto, Shinagawa-ku (JP); Akimichi Morita, Nagoya (JP)

(73) Assignees: NEC Lighting, Ltd, Tokyo (JP); Public University Corporation Nagoya City University, Aichi (JP)

( * ) Notice: Subject to any disclaimer, the term of this patent is extended or adjusted under 35 U.S.C. 154(b) by 1187 days.

(21) Appl. No.: 11/230,269

(22) Filed: Sep. 20, 2005

(65) Prior Publication Data

US 2006/0195166 A1 Aug. 31, 2006

(30) Foreign Application Priority Data

Sep. 21, 2004 (JP) ................................. 2004-273221

(51) Int. Cl.
*A61N 5/06* (2006.01)
(52) U.S. Cl. ................. 607/94; 607/88; 607/90; 606/10
(58) Field of Classification Search .................... 607/94, 607/88–91, 93; 602/2, 9; 362/84, 260, 321, 362/324, 804; 250/504, 483.1, 493.1; 606/3, 606/8, 9–12

See application file for complete search history.

(56) References Cited

U.S. PATENT DOCUMENTS

| 2,205,179 | A | * | 6/1940 | Schultz | 359/889 |
| 3,455,634 | A | * | 7/1969 | Guffon | 355/91 |
| 4,017,176 | A | * | 4/1977 | Beguin et al. | 355/32 |
| 4,558,700 | A | * | 12/1985 | Mutzhas | 607/94 |
| 5,300,097 | A | * | 4/1994 | Lerner et al. | 607/93 |
| 5,720,772 | A | * | 2/1998 | Eckhouse | 607/88 |
| 5,961,543 | A | * | 10/1999 | Waldmann | 607/88 |
| 6,413,268 | B1 | * | 7/2002 | Hartman | 607/94 |
| 6,447,537 | B1 | * | 9/2002 | Hartman | 607/94 |
| 6,881,964 | B2 | * | 4/2005 | Holmes | 250/492.1 |
| 7,276,059 | B2 | * | 10/2007 | Irwin | 606/9 |
| 2007/0135872 | A1 | * | 6/2007 | Sumitomo et al. | 607/90 |
| 2010/0145321 | A1 | * | 6/2010 | Altshuler et al. | 606/9 |

FOREIGN PATENT DOCUMENTS

| DE | 76 13 630 | | 11/1976 |
| DE | 33 26 513 A1 | | 1/1985 |
| EP | 1 067 166 A2 | | 1/2001 |
| JP | 07 088113 A | | 4/1995 |
| JP | 07-088113 A | | 4/1995 |
| JP | 7-88113 A | | 4/1995 |
| JP | 2004-350946 A | | 12/2004 |
| KR | 2002-91373 A | | 12/2002 |
| WO | WO 8500527 A1 | * | 2/1985 |
| WO | 02/055149 A2 | | 7/2002 |

* cited by examiner

*Primary Examiner* — Ahmed M Farah
(74) *Attorney, Agent, or Firm* — Sughrue Mion, PLLC (57) ABSTRACT

An instrument for ultraviolet irradiation includes a plurality of light-shielding filters each having different transmittances for ultraviolet radiation emitted from a light source for irradiating the skin of a patient with ultraviolet radiation, and a support member for supporting the light-shielding filters.

17 Claims, 6 Drawing Sheets

Fig. 6

INSTRUMENT FOR ULTRAVIOLET IRRADIATION AND ULTRAVIOLET IRRADIATING APPARATUS

BACKGROUND OF THE INVENTION

1. Field of the Invention

The present invention relates to an instrument for ultraviolet irradiation and an ultraviolet irradiating apparatus for irradiating the skin with an ultraviolet radiation emitted from a light source to determine the minimum erythema dose or treat the skin according to dermatological procedures.

2. Description of the Related Art

For treating photosensitive diseases in accordance with dermatological practices, the minimum erythema dose (MED) to the skin of each patient needs to be calculated. The minimum erythema dose is judged as follows: A plurality of irradiated areas or spots are formed on the skin of the patient by means of irradiation with different levels of ultraviolet radiation intensity, and the state of the skin in each of the spots is visually examined by the doctor.

One conventional ultraviolet radiation applying apparatus that is used to form a plurality of spots with different ultraviolet radiation intensities is disclosed in Japanese laid-open patent publication No. 7-88113, for example. The disclosed conventional ultraviolet radiation applying apparatus has a plurality of holes through which pass ultraviolet radiation emitted from a light source device that is separate from the ultraviolet radiation applying apparatus, and an exposure unit having a shutter for successively opening and closing the holes one by one.

The conventional ultraviolet radiation applying apparatus operates as follows: While the ultraviolet radiation is being emitted from the light source device, the shutter is intermittently moved to successively open and close the holes one by one to form a succession of spots with different ultraviolet radiation intensities. The doctor is kept away from the patient who is irradiated with the ultraviolet radiation by the light source device, and remotely controls the shutter mechanism. Therefore, the doctor is prevented from being exposed to the ultraviolet radiation.

The light source device that is used in combination with the conventional ultraviolet radiation applying apparatus is generally used to treat the patient by applying ultraviolet radiation, and is installed in a dedicated irradiation chamber which is dedicated to irradiate the patient with ultraviolet radiation. To measure the minimum erythema dose that is to be administered to the patient is accomplished by having the patient remain in the chamber and holds the ultraviolet radiation applying apparatus over the region of the body that is to be irradiated with ultraviolet radiation, then a plurality of spots are formed on the body region by the ultraviolet radiation that has been applied. Therefore, the conventional ultraviolet radiation applying apparatus is disadvantageous in that the body region where the spots are formed for measuring the minimum erythema dose as well as other body regions of the patient are exposed to the ultraviolet radiation emitted from the light source device.

Measuring the minimum erythema dose with the conventional ultraviolet radiation applying apparatus, it is necessary to provide a dedicated irradiation chamber in which the ultraviolet radiation applying apparatus is installed, and a shield needs to be installed to block the ultraviolet radiation emitted from the light source device. Accordingly, the conventional ultraviolet radiation applying apparatus requires sufficient installation space for measurement.

With the conventional ultraviolet radiation applying apparatus, furthermore, when the patient is irradiated with ultraviolet radiation, the doctor is required to operate the light source device, and needs remain away from the patient who is irradiated with the ultraviolet radiation by the light source device, or needs to be protected by the shield against exposure to the ultraviolet radiation emitted from the light source device. Consequently, the process of measuring the minimum erythema dose with conventional ultraviolet radiation applying apparatus has been relatively complex to perform.

SUMMARY OF THE INVENTION

It is an object of the present invention to provide an instrument for ultraviolet irradiation and an ultraviolet irradiating apparatus that can easily form a plurality of areas or spots on the skin of a patient by irradiating the patient with different ultraviolet radiation intensities.

To achieve the above object, an instrument for ultraviolet irradiation according to the present invention includes a plurality of light-shielding filters each having different ultraviolet radiation transmittances for ultraviolet radiation emitted from a light source to irradiate the skin of the patient with ultraviolet radiation, and a support member for supporting the light-shielding filters.

With the above instrument for ultraviolet irradiation, the ultraviolet radiation emitted from the light source passes through the light-shielding filters and forms a plurality of irradiated areas that correspond to the light-shielding filters with each area having a different ultraviolet radiation intensity. The instrument for ultraviolet irradiation thus makes it possible to easily form a plurality of irradiated areas with different ultraviolet radiation intensities. Since it is not necessary for the instrument to block the ultraviolet radiation mechanically, the instrument is simple in structure, small in size, and low in profile.

The instrument should preferably include a land disposed close to the light-shielding filters and projecting along the optical axis of ultraviolet irradiation from the area surrounding the light-shielding filter. When the land is held against the skin of the patient, it can be easily and stably maintained on the irradiated position of the skin with high accuracy.

An ultraviolet irradiating apparatus according to the present invention includes a light source for irradiating the skin of the patient with ultraviolet radiation, and a plurality of light-shielding filters each having different ultraviolet radiation transmittances for the ultraviolet radiation emitted from the light source.

As the ultraviolet irradiating apparatus does not have a separate light source device, no installation space is needed for such a separate light source device. When the ultraviolet radiation emitted from the light source passes through the light-shielding filters, it easily forms a plurality of irradiated areas with different ultraviolet radiation intensities.

The ultraviolet irradiating apparatus should preferably include a land disposed close to the light-shielding filters and projecting along the optical axis of ultraviolet irradiation from the area surrounding the light-shielding filter. The land is effective to prevent the ultraviolet radiation that has passed through the light-shielding filters from leaking out of the irradiated areas that are formed. When the land is held against the skin of the patient, it can be easily and stably maintained on the irradiated position of the skin with high accuracy.

The light source of the ultraviolet irradiating apparatus should preferably be of a flat structure having a pair of panels each having an ultraviolet-emission fluorescent layer. The light source thus constructed can emit ultraviolet radiation at a sufficiently high level of intensity, provide ultraviolet radiation at a uniform level of intensity in each of irradiated areas, and quickly emit ultraviolet radiation at a desired intensity when turned on. Furthermore, the ultraviolet irradiating apparatus is small in size and low in profile.

The ultraviolet irradiating apparatus should preferably include shutter means having a shutter unit movable between a closed position in which the shutter unit blocks the ultraviolet radiation from the light source and an open position in which the shutter unit allows the ultraviolet radiation from the light source to be applied. When the shutter unit is moved from the open position to the closed position, it reliably blocks the ultraviolet radiation from the light source.

The ultraviolet irradiating apparatus may have a cover for blocking ultraviolet radiation from at least one of the light-shielding filters. When one or more of the light-shielding filters are not used, they are covered by the cover to block ultraviolet radiation from them. Accordingly, the number of light-shielding filters to be used can be adjusted.

According to the present invention, the ultraviolet radiation emitted from the light source is blocked optically, rather than mechanically, by the light-shielding filters each having different ultraviolet radiation transmittances to thereby easily form a plurality of irradiated areas with different ultraviolet radiation intensities.

The above and other objects, features, and advantages of the present invention will become apparent from the following description with reference to the accompanying drawings which illustrate examples of the present invention.

DESCRIPTION OF THE PREFERRED EMBODIMENTS

An ultraviolet irradiating apparatus according to an embodiment of the present invention can be used as an apparatus to examine the minimum erythema dose (MED) applied to the skin of a patient, and can also be used as a light therapy apparatus.

Figure 1:
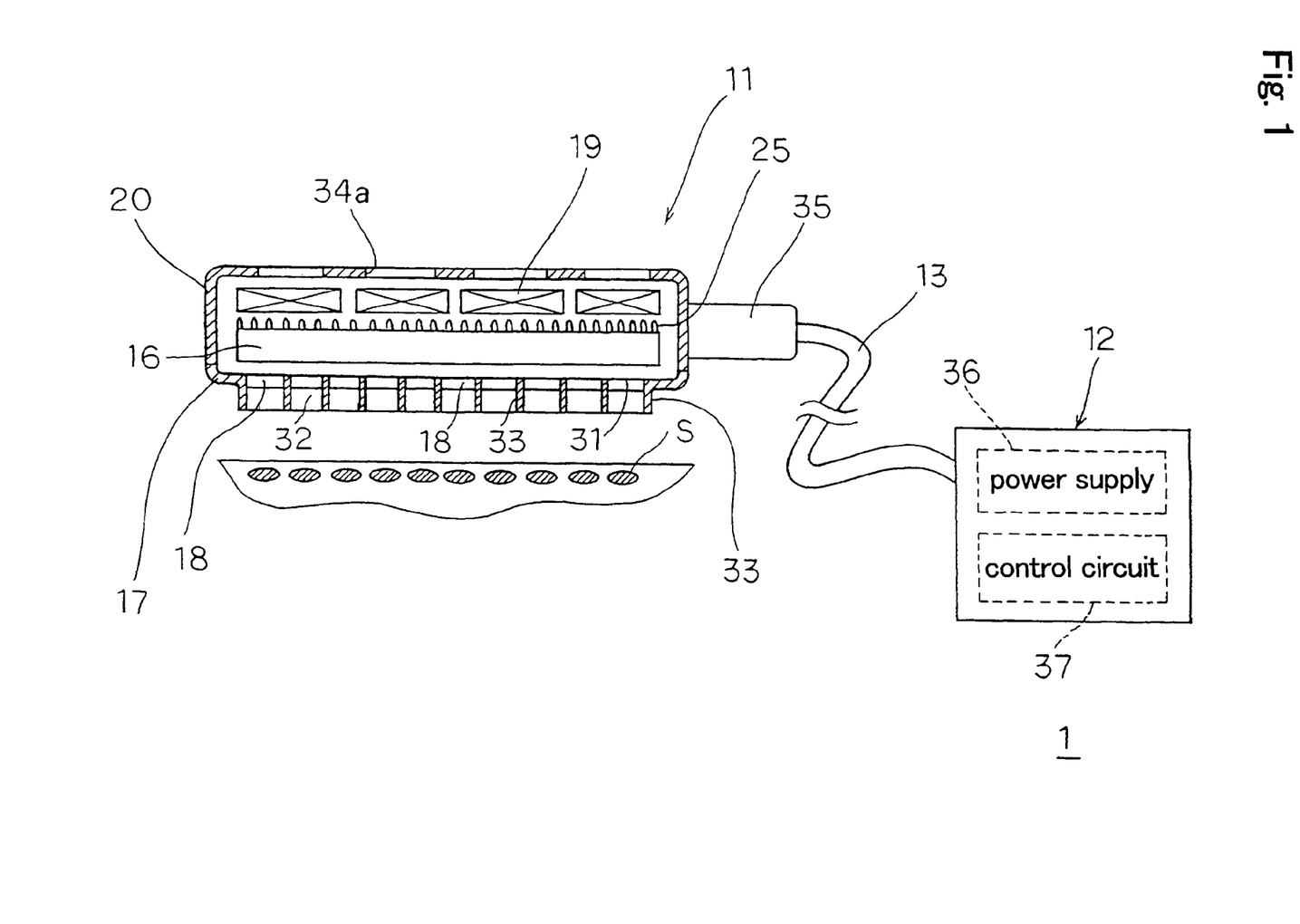
FIG. 1 is a view, partly in cross section, of an ultraviolet irradiating apparatus according to an embodiment of the present invention.

As shown in FIG. 1, ultraviolet irradiating apparatus 1 according to an embodiment of the present invention has ultraviolet irradiator 11 for applying ultraviolet radiation, controller 12 for controlling the operation of ultraviolet irradiator 11, and connecting cable 13 for electrically connecting ultraviolet irradiator 11 and controller 12 to each other.

Figure 2:
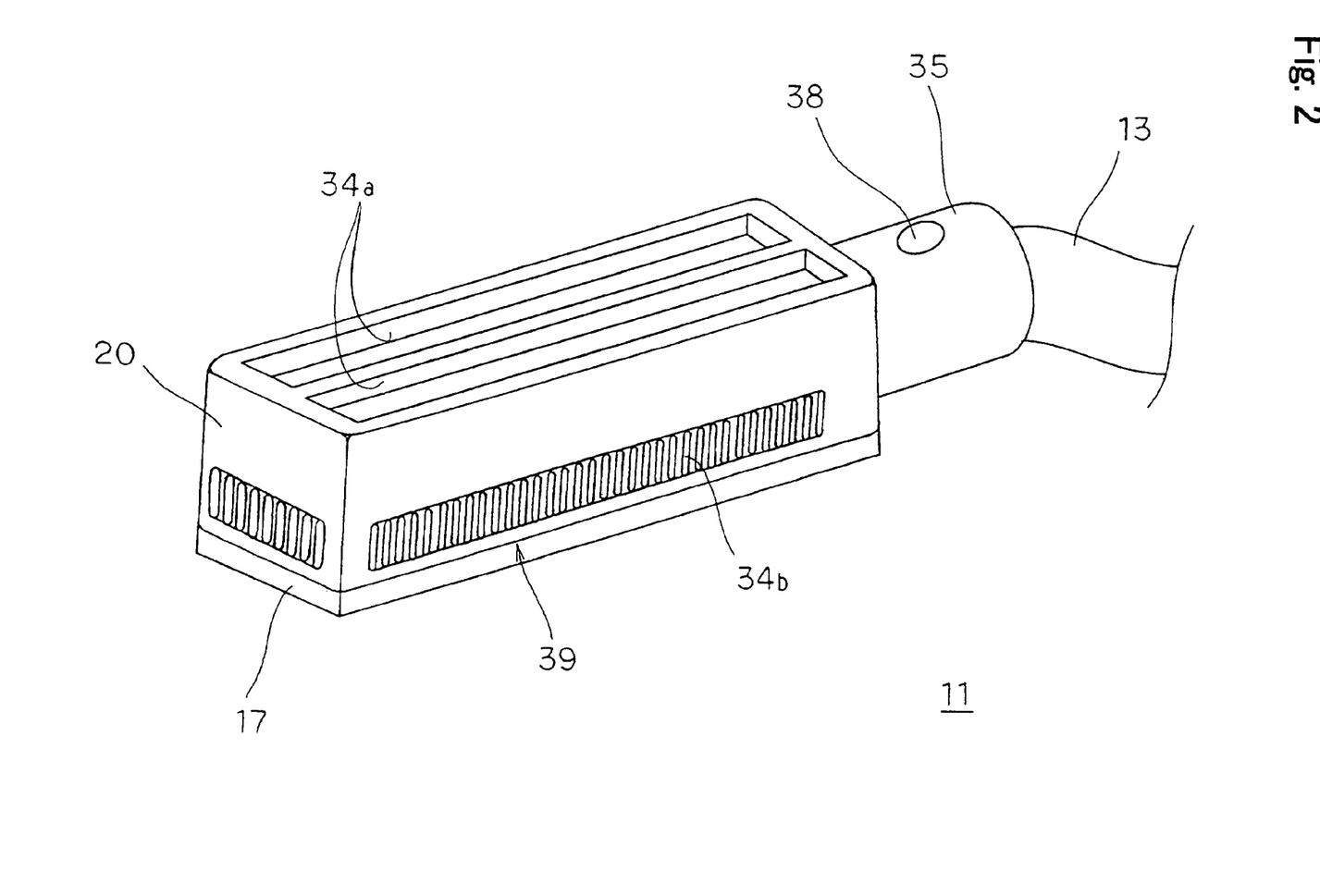
FIG. 2 is a perspective view of an ultraviolet irradiator of the ultraviolet radiation applying apparatus.
Figure 3:
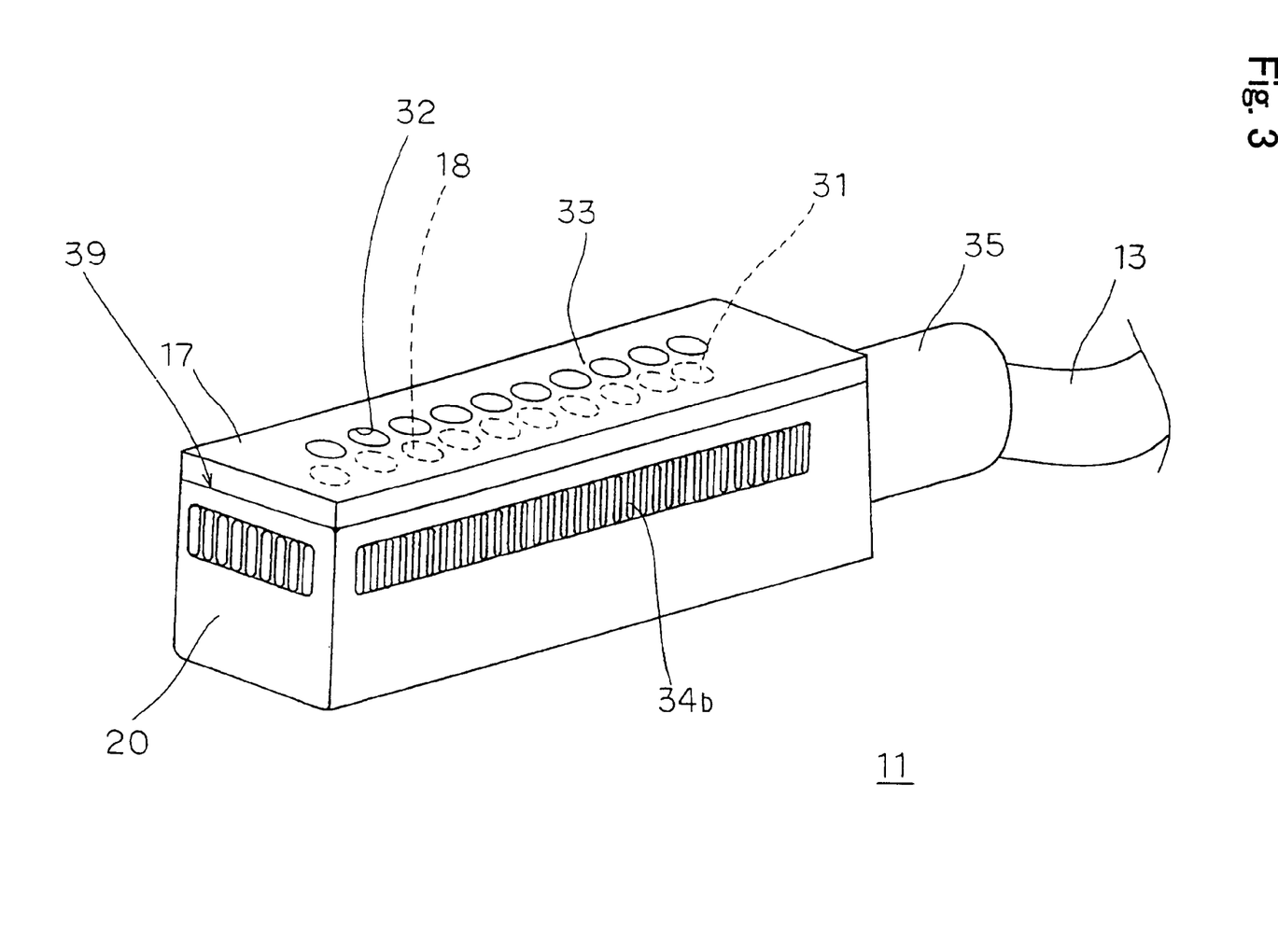
FIG. 3 is a perspective view of the ultraviolet irradiator.

As also shown in FIGS. 2 and 3, ultraviolet irradiator 11 comprises light source 16 for applying ultraviolet radiation to the skin of a patient, filter unit 17 having a plurality of light-shielding filters 18 each having different ultraviolet radiation transmittances for the ultraviolet radiation emitted from light source 16, cooling mechanism 19 for cooling light source 16, and casing 20 for covering light source 16, and cooling mechanism 19 and supporting filter unit 17.

Figure 4A:
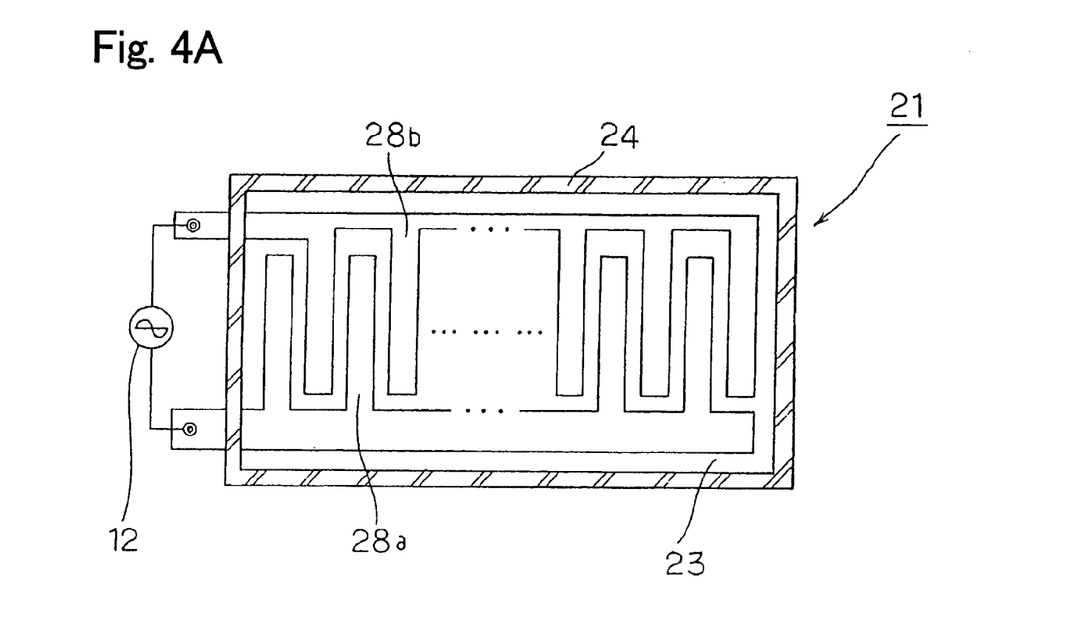
FIG. 4A is a horizontal cross-sectional view of an ultraviolet fluorescent lamp of a light source in the ultraviolet irradiator.
Figure 4B:
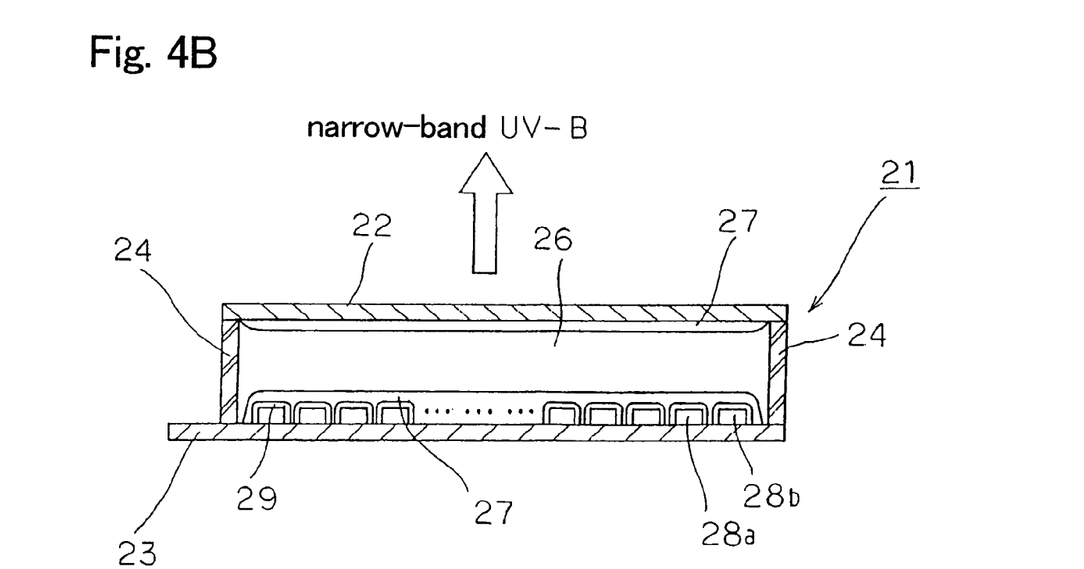
FIG. 4B is a vertical cross-sectional view of the ultraviolet fluorescent lamp of the light source.

As shown in FIGS. 4A and 4B, light source 16 has ultraviolet fluorescent lamp 21 for emitting narrow-band ultraviolet radiation (UV-B). Ultraviolet fluorescent lamp 21 is of a flat structure having a pair of ultraviolet transmitting panel 22 and rear panel 23 which are positioned to face each other, and sealing frame 24 interposed between ultraviolet transmitting panel 22 and rear panel 23 and enclosing the space therebetween.

Sealing frame 24 is made of glass and extends along the outer peripheral edges of ultraviolet transmitting panel 22 and rear panel 23. Ultraviolet transmitting panel 22, rear panel 23, and sealing frame 24 jointly define hermetically sealed discharge chamber 26 in ultraviolet fluorescent lamp 21. Discharge chamber 26 is filled with a discharge medium comprising a gas such as xenon or a mixed gas such as a mixture of xenon and another rare gas such as neon, argon, or the like, for example. The gas comprises a 100% rare gas and does not contain a mercury vapor unlike a mercury-vapor ultraviolet fluorescent lamp used as a light source for conventional narrow-band ultraviolet therapy apparatus. Therefore, ultraviolet fluorescent lamp 21 is environmentally friendly and is capable of quickly emitting ultraviolet radiation. Ultraviolet fluorescent lamp 21 can emit ultraviolet radiation at a sufficiently high level of intensity, provide ultraviolet radiation at a uniform level of intensity in each of irradiated spots S on the skin of the patient, and quickly emit ultraviolet radiation at a desired intensity when turned on.

Ultraviolet transmitting panel 22 is made of ultraviolet-transmissive glass for transmitting radiations having wavelengths of 300 nm and longer therethrough. As shown in FIG. 4B, ultraviolet-emission fluorescent layer 27 is disposed on the inner surface of ultraviolet transmitting panel 22 which faces discharge chamber 26. Ultraviolet-emission fluorescent layer 27 is made of $YF_3$:Gd (gadolinium) for vacuum ultraviolet excitation, Pr (praseodymium) fluorescent material, $YBO_3$:Gd,Pr fluorescent material, $YB_xO_y$:Gd,Pr fluorescent material, (where X, Y represent a desired integer), $(Y_{1-X}Gd_X)Al_3(BO_3)_4$ (where $0 \leq X \leq 1$) fluorescent material, or a mixture of the above fluorescent materials. Ultraviolet-emission fluorescent layer 27 has a thickness in the range from about 20 µm to 50 µm, for example. Ultraviolet-emission fluorescent layer 27 is excited by an ultraviolet radiation having a wavelength of 147 nm which is emitted by a xenon discharge, for example, and emits a narrow-band ultraviolet radiation (UV-B) having an emission spectrum with a sharp peak that is in the vicinity of the wavelength of 310 nm. The sharp peak that is in the vicinity of the wavelength of 310 nm refers to a peak having a half-value width of about 5 nm at 313 nm, for example. Ultraviolet-emission fluorescent layer 27 may not contain Pr insofar as it is made of a fluorescent material with Gd added thereto and is capable of emitting a narrow-band ultraviolet radiation (UV-B).

As shown in FIG. 4A, a pair of electrodes 28a, 28b is mounted on the inner surface of rear panel 23 which faces discharge chamber 26. Electrodes 28a, 28b, each having a combtoothed planar shape, are combined in interdigitating relation to each other. A dielectric layer 29 made primarily of silica is disposed on electrodes 28a, 28b, and is covered with ultraviolet-emission fluorescent layer 27 which is identical to ultraviolet-emission fluorescent layer 27 disposed on ultraviolet transmitting panel 22.

As shown in FIG. 1, a plurality of heat-radiating fins 25 for radiating the heat of ultraviolet fluorescent lamp 21 are mounted on rear panel 23. Heat-radiating fins 25 are disposed in a position that faces cooling mechanism 19, and radiates the heat effectively through cooling mechanism 19.

Electrodes 28a, 28b are formed to a desired pattern by screen printing using electrically conductive paste that is made up of a material having relatively high electric conductivity such as of silver, gold, or the like. Because electrodes 28a, 28b are formed by screen printing, they can be shaped to minute configurations. For example, the widths of the teeth of electrodes 28a, 28b and the distances (pitch) between each of the adjacent teeth of electrodes 28a, 28b can be easily set to several tens μm. Electrodes 28a, 28b may alternatively be formed of a thin electrically conductive film by sputtering and shaped by photolithography. If electrodes 28a, 28b are formed by sputtering and photolithography, then the widths of the teeth of electrodes 28a, 28b and the distances (pitch) between each of the adjacent teeth of electrodes 28a, 28b may be set to the order of μm or less. Electrodes 28a, 28b thus formed are small in size and low in profile, but enable ultraviolet fluorescent lamp 21 to emit ultraviolet radiation at a sufficiently high intensity level.

In operation, an inverter (not shown) in power supply 36, described later, of controller 12 applies a high AC voltage of several kV, which may be a sine-wave or rectangular-wave voltage, between electrodes 28a, 28b of ultraviolet fluorescent lamp 21. When high AC voltage is applied between electrodes 28a, 28b, dielectric layer 29 produces a dielectric barrier discharge in discharge chamber 26, causing the discharge medium of xenon to radiate ultraviolet radiation. The ultraviolet radiation, whose wavelengths are primarily 147 nm and 172 nm, excites each ultraviolet-emission fluorescent layer 27 to emit narrow-band ultraviolet radiation (UV-B) having an emission spectrum with a sharp peak in the vicinity of the wavelength of 310 nm.

Filter unit 17 is removably mounted on filter mount 39, described later, on one side of casing 20. Filter unit 17 has nine light-shielding filters 18 having respective different transmittances for the ultraviolet radiation emitted from light source 16 and single circular opening 31 that does not have any light-shielding filters, and ultraviolet radiation emitted from light source 16 will pass through it. The transmittances for the ultraviolet radiation of light-shielding filters 18 range from 10% to 90% at intervals of 10%, and the transmittance for the ultraviolet radiation of opening 31 is 100%. Light-shielding filters 18 and opening 31 are linearly arrayed such that their transmittances for the ultraviolet radiation are successively arranged from 10% to 100%.

When the ultraviolet radiation emitted from light source 16 is applied through filter unit 17 to the skin of the patient, ten circular spots S (see FIG. 1) are formed on the skin of the patient with different ultraviolet radiation intensities for the ultraviolet radiation that has passed through each of light-shielding filters 18 and opening 31. Spots S, each having a diameter in the range from 5 mm to 30 mm, are linearly arrayed such that the intensities of the ultraviolet radiation applied thereto are progressively greater from one end toward the other end of filter unit 17.

Filter unit 17 may have an adjusted number of light-shielding filters 18 such that 10 to 20 spots S may be formed on the skin of the patient by light-shielding filters 18 and opening 31 with different ultraviolet radiation intensities depending on the purpose of examination. Though light-shielding filters 18 and opening 31 are shown as being linearly arrayed, they may be arranged in any of various different patterns, e.g., a pattern represented by a plurality of columns, a pattern represented by a plurality of radial arms, a pattern represented by a circle, etc.

Each of light-shielding filters 18 comprises a circular glass plate having a diameter in the range from 5 mm to 30 mm or a square glass plate having sides each with a length in the range from 5 mm to 30 mm, and a film of chromium having a desired thickness deposited on a surface of the glass plate. The amount of radiation that is transmitted through each light-shielding filter 18 is controlled by the thickness of the film of chromium. For example, each of light-shielding filters 18 may be a reflective fixed ND filter manufactured by SIGMA KOKI CO., LTD. Alternatively, each of light-shielding filters 18 may be an optical filter comprising a glass plate with a plurality of dot-like dents defined in a surface thereof for causing diffused reflection to change the ultraviolet radiation transmittance in the vicinity of the wavelength of 310 nm.

Filter unit 17 has integral continuous land 33 disposed around light-shielding filters 18 and opening 31 and projecting substantially parallel to the optical axis of the ultraviolet radiation that passes through light-shielding filters 18 and opening 31. Land 33 has through holes 32 defined therein in alignment with light-shielding filters 18 and opening 31, respectively, which are disposed in respective inner ends of through holes 32. Therefore, the ultraviolet radiation that has passed through light-shielding filters 18 and opening 31 is prevented from leaking out of spots S by inner wall surfaces of through holes 32.

In use, land 33 of filter unit 17 is held against the skin of the patient to position ultraviolet irradiator 11 with respect to the region to be irradiated of the skin. Since the irradiated position on the skin is thus stably and easily maintained, spots S formed on the skin by the ultraviolet radiation applied by ultraviolet irradiator 11 are prevented from being displaced in position. Therefore, the accuracy of the irradiated position on the skin is high. The surface of land 33 to be held against the skin of the patient may be curved complementarily to the average shape of skin regions to be irradiated with the ultraviolet radiation for thereby further increasing the stability of filter unit 17 held against the skin and the accuracy of the irradiated position on the skin.

Land 33 is illustrated as being integral with filter unit 17 and having through holes 32. However, a tubular or flat shield wall for preventing the ultraviolet radiation from leaking out of spots S may be perpendicularly mounted on filter unit 17 in surrounding relation to light-shielding filters 18 and opening 31. In the above illustrated embodiment, filter unit 17 has light-shielding filters 18 and opening 31. However, filter unit 17 may only have light-shielding filters 18, and an opening through which ultraviolet radiation directly passes from light source 16, may be provided separately from filter unit 17.

Since filter unit 17 is removably mounted on filter mount 39 on one side of casing 20, as described above, filter unit 17 may easily be replaced with another filter unit comprising light-shielding filters each having different ultraviolet radiation transmittances for the ultraviolet radiation emitted from light source 16.

Cooling mechanism 19 is disposed adjacent to light source 16 within casing 20. Although not shown, cooling mechanism 19 has a plurality of cooling fans and a plurality of drive motors for rotating the cooling fans, respectively. As shown in FIGS. 1 and 2, casing 20 has air outlet ports 34a defined in an upper wall thereof remote from filter unit 17 in alignment with the cooling fans, respectively, and slit-like air inlet ports 34b defined in the side walls of casing 20.

As shown in FIGS. 2 and 3, filter mount 39 on which filter unit 17 is removably mounted is disposed on one side of casing 20 remote from air outlet ports 34a. Grip handle 35 to be gripped by the user is mounted on a longitudinal end wall of casing 20. Connecting cable 13 has an end portion extending through grip handle 35. Grip handle 35 has operating button 38 to be pressed by the user for energizing light source 16. Operating button 38 is combined with a switch (not shown) housed in grip handle 35 and electrically connected to controller 12.

Controller 12 has power supply 36 for supplying electric energy to light source 16 and cooling mechanism 19, and control circuit 37 for controlling energization of light source 16. Control circuit 37 has a timer circuit which automatically de-energizes ultraviolet fluorescent lamp 21 after the elapse of a preset period of time from the time when ultraviolet fluorescent lamp 21 was energized by pressing operating button 38.

A process for forming a plurality of spots S on the skin of the patient with different ultraviolet radiation intensities, using ultraviolet irradiating apparatus 1, will be described below.

First, land 33 of ultraviolet irradiator 11 is held against the skin of a region to be irradiated, such as an arm, abdomen, or the like.

Then, operating button 38 is pressed by the user to energize ultraviolet fluorescent lamp 21 of light source 16, which emits an ultraviolet radiation having a desired intensity. The ultraviolet radiation passes through light-shielding filters 18 and opening 31 of filter unit 17, and is applied to the skin of the patient at spots S with different levels of ultraviolet radiation intensity. Because land 33 held against the skin of the patient prevents the applied ultraviolet radiation from leaking out of spots S, regions of the patient other than the irradiated region are not irradiated with the ultraviolet radiation, and the doctor is also protected from undue exposure to the ultraviolet radiation though the doctor remains close to the patient.

After elapse of a predetermined period of time from the energization of ultraviolet fluorescent lamp 21, the timer circuit of control circuit 37 of controller 12 automatically de-energizes ultraviolet fluorescent lamp 21, thereby forming spots S on the skin of the patient with different levels of ultraviolet radiation intensity. The state of the skin in each of spots S is visually examined by the doctor to determine the minimum erythema dose.

Since ultraviolet irradiating apparatus 1 has filter unit 17 with light-shielding filters 18 and opening 31 each having different ultraviolet radiation transmittances for the ultraviolet radiation that is emitted from light source 16, it does not need to have a mechanical unit, and can easily form spots S on the skin of the patient with different levels of ultraviolet radiation intensity, optically with light-shielding filters 18 and opening 31 in a relatively short period of time. Because ultraviolet irradiating apparatus 1 does not have a separate light source device and hence requires no installation space for such a separate light source device, ultraviolet irradiating apparatus 1 is small in size and low in profile.

Since land 33 with through holes 32 defined therein prevents ultraviolet radiation which passes through light-shielding filters 18 and opening 31 from leaking out of spots S, regions of the patient other than the irradiated region are not irradiated with ultraviolet radiation, and the doctor is also protected from undue exposure to ultraviolet radiation though the doctor is not kept away from the patient. Because of land 33, it is not necessary to provide a separate shield to block the ultraviolet radiation from light source 16 in order to protect the doctor against undue exposure. In addition, as ultraviolet irradiator 11 is stably kept in position when land 33 is held against the skin of the patient, the accuracy of the irradiated position at spots S on the skin is increased.

Inasmuch as light source 16 has ultraviolet fluorescent lamp 21 which has flat structure, light source 16 can emit ultraviolet radiation at a sufficiently high level of intensity, provide ultraviolet radiation at a uniform level of intensity in each of irradiated spots S on the skin of the patient, and quickly emit ultraviolet radiation at a desired level of intensity when turned on. Furthermore, ultraviolet irradiating apparatus 1 is small in size and low in profile.

After the minimum erythema dose has been diagnosed from the state of each of spots S, filter unit 17 can be removed from casing 20, allowing the ultraviolet radiation emitted from light source 16 to be applied directly to the skin of the patient. Therefore, ultraviolet irradiating apparatus 1 can be used as a light therapy apparatus to treat the skin of the patient by directly applying the ultraviolet radiation emitted from light source 16 thereto.

Other embodiments of the present invention will be described below. Those parts of the other embodiments which are identical to those of ultraviolet irradiating apparatus 1 according to the above embodiment are denoted by identical reference characters, and will not be described in detail below.

According to the above embodiment, control circuit 37 of controller 12 controls the period of time in which the ultraviolet radiation is applied to the skin of the patient by turning ultraviolet fluorescent lamp 21 on and off based on the period of time that has elapsed. According to another embodiment of the present invention, the ultraviolet irradiator has a shutter plate for blocking the ultraviolet radiation from the light-shielding shutters in order to control the period of time in which the ultraviolet radiation is applied to the skin of the patient.

Figure 5:
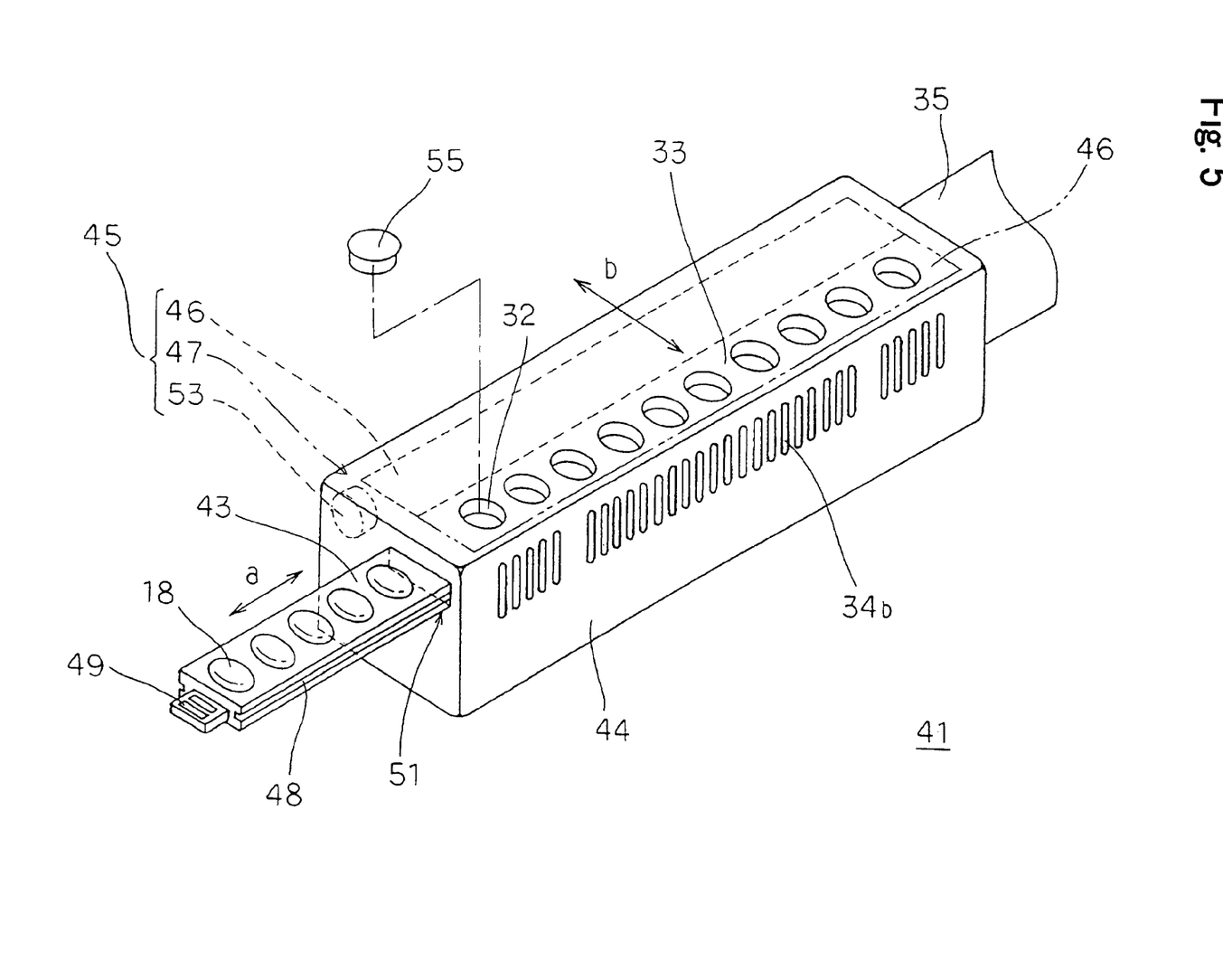
FIG. 5 is a perspective view of an ultraviolet irradiator according to another embodiment of the present invention.

As shown in FIG. 5, an ultraviolet irradiating apparatus according to another embodiment of the present invention has ultraviolet irradiator 41 for applying ultraviolet radiation to the skin of the patient and controller 12 (see FIG. 1) for controlling the operation of ultraviolet irradiator 41.

Ultraviolet irradiator 41 comprises filter unit 43 having a plurality of light-shielding filters 18 and opening 31 each having different ultraviolet radiation transmittances for the ultraviolet radiation that is emitted from light source 16, casing 44 which supports therein filter unit 43 for movement in the directions indicated by the arrow "a" which are parallel to the longitudinal axis of casing 44, and shutter mechanism 45 having shutter plate 46 for selectively blocking the ultraviolet radiation that has passed through light-shielding filters 18 and opening 31.

Filter unit 43 is substantially in the form of an elongate flat plate having light-shielding filters 18 and opening 31. Filter unit 43 has guide grooves 48 defined in and along respective opposite longitudinal edges thereof. Casing 44 has filter mount 51 in the form of an elongate slot defined therein and guide rails (not shown) extending on opposite side walls of filter mount 51. The guide rails slidably ride in respective guide grooves 48 so that filter unit 43 can move in filter mount 51 along guide rails. Filter unit 43 has grip tab 49 disposed on one longitudinal end thereof for being gripped when filter unit 43 is to be inserted into and removed from filter mount 51.

Filter mount 51 has an end open at one end of casing 44, and filter unit 43 can be inserted into and removed from filter mount 51 through the open end thereof.

Shutter plate 46 is movable in casing 44 in the directions indicated by arrow "b" which are perpendicular to the directions indicated by arrow "a". Shutter mechanism 45 has actuator mechanism 47 for moving shutter plate 46 in the directions indicated by arrow "b". Shutter plate 46 is of such a size that it can completely cover light-shielding filters 18 and opening 31 when they are aligned with through holes 32 defined in land 33 of casing 44. Shutter plate 46 is movable between a closed position in which it closes through holes 32 to block ultraviolet radiation from light-shielding filters 18 and opening 31, and an open position in which it opens through holes 32 to allow ultraviolet radiation to pass from light-shielding filters 18 and opening 31. Actuating mechanism 47 has motor 53 for actuating a gear train (not shown) held in a driving mesh with shutter plate 46.

The timer circuit of control circuit 37 of controller 12 operates to energize motor 53 to move shutter plate 46 thereby controlling the period of time in which ultraviolet radiation is applied from light-shielding filters 18 and opening 31. Shutter plate 46 is also effective in preventing dust particles from being applied to light-shielding filters 18 and also from entering ultraviolet irradiator 41. Shutter plate 46 may be arranged to move into a position between light source 16 and light-shielding filters 18 and opening 31 in order to block the ultraviolet radiation from light source 16.

Ultraviolet irradiator 41 has cap 55 serving as a cover that can be fitted into either one of through holes 32 defined in land 33 to prevent the ultraviolet radiation that has passed through a corresponding one of light-shielding filters 18 and opening 31. Cap 55 is in the form of a bottomed hollow cylindrical body made of synthetic resin or the like. When cap 55 is placed in either one of through holes 32, it blocks the ultraviolet radiation that has passed through a corresponding one of light-shielding filters 18 and opening 31. A desired number of caps 55 may be placed respectively in through holes 32 to adjust the number of spots S to be formed so that spots S will not be formed in body regions that should not be irradiated with ultraviolet radiation.

After the elapse of a predetermined period of time from the opening of shutter plate 46, the timer circuit of control circuit 37 energizes motor 53 to move shutter plate 46 into the closed position, closing light-shielding filters 18 and opening 31. The timer circuit of control circuit 37 may control the energization time of ultraviolet fluorescent lamp 21 as well as the movement of shutter plate 46.

While light-shielding filters 18 and opening 31 are being completely closed by shutter plate 46, land 33 of ultraviolet irradiator 41 is held against the skin of the patient.

Then, control circuit 37 of controller 12 energizes ultraviolet fluorescent lamp 21, and controls shutter mechanism 45 to move shutter plate 46 into the open position, thereby initiating application of ultraviolet radiation, that has passed through light-shielding filters 18 and opening 31, to the skin of the patient.

After a predetermined period of time has elapsed from the opening of shutter plate 46, the timer circuit of control circuit 37 energizes motor 53 to move shutter plate 46 into the closed position, thereby blocking the ultraviolet radiation from passing through light-shielding filters 18 and opening 31. The timer circuit of control circuit 37 also automatically de-energizes ultraviolet fluorescent lamp 21. In this manner, spots S are formed on the skin of the patient with different levels of ultraviolet radiation intensity.

Together with ultraviolet irradiator 41 according to the embodiment shown in FIG. 5, shutter mechanism 45 having shutter plate 46 for selectively blocking the ultraviolet radiation from passing through light-shielding filters 18 and opening 31, is capable of controlling the period of time in which the ultraviolet radiation from light source 16 is applied.

When filter unit 43 is slid in the directions indicated by arrow "a", filter unit 43 can easily be inserted into and removed from filter mount 51 in casing 44. Accordingly, filter unit 43 can be replaced with another filter unit.

According to the above embodiments, the ultraviolet irradiating apparatus has a light source for emitting ultraviolet radiation. According to still another embodiment of the present invention, an instrument for ultraviolet irradiation serves to form spots S on the skin of the patient with different levels of ultraviolet radiation intensity from another light source device.

Figure 6:
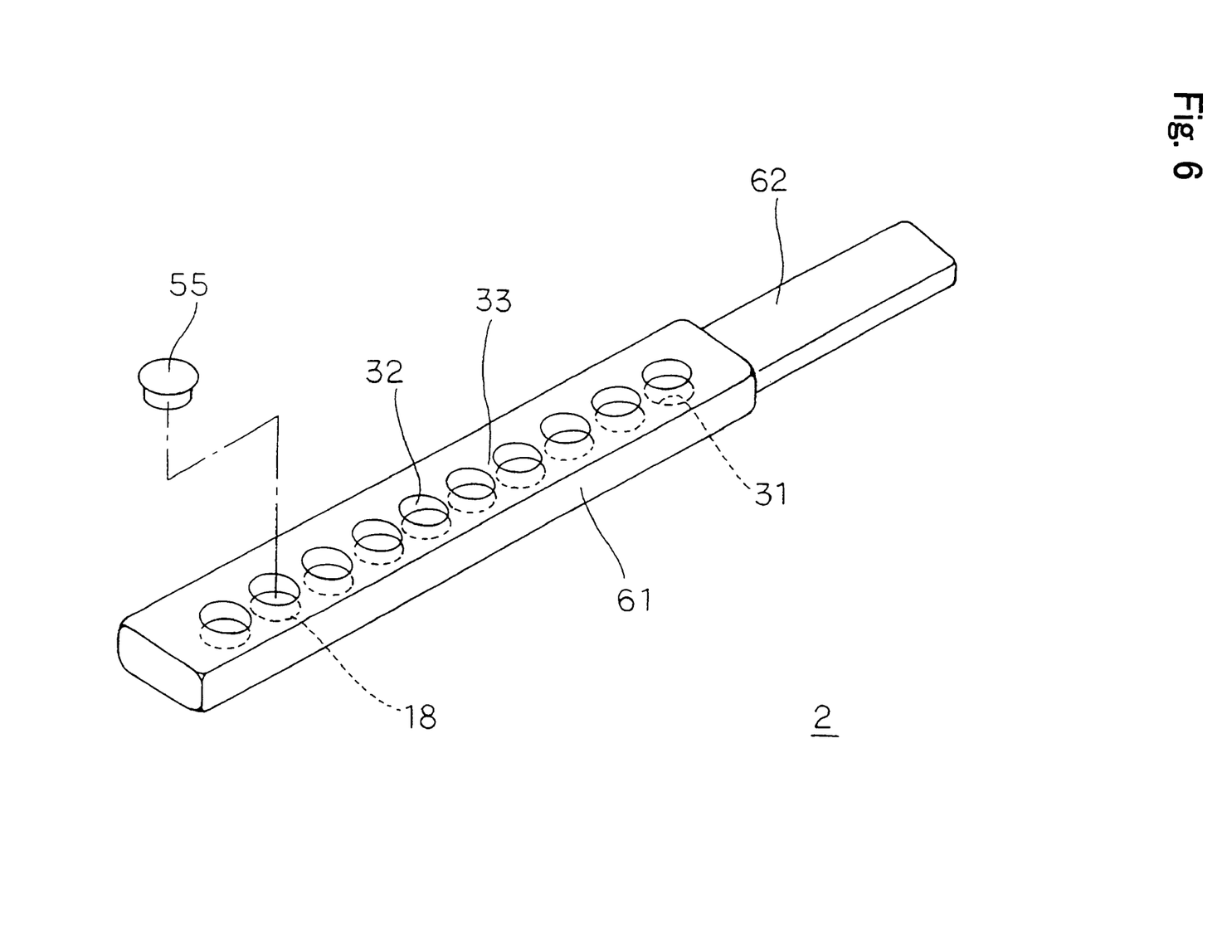
FIG. 6 is a perspective view of an instrument for ultraviolet irradiation according to still another embodiment of the present invention.

As shown in FIG. 6, instrument 2 for ultraviolet irradiation according to still another embodiment of the present invention comprises a plurality of light-shielding filters 18 each having different ultraviolet radiation transmittances, and support bar 61 to support light-shielding filters 18 thereon. Support bar 61 also has opening 31 defined therein near an end of the array of light-shielding filters 18. Grip handle 62 to be gripped by the doctor is mounted on the longitudinal end of support bar 61.

Instrument 2 for ultraviolet irradiation is essentially equivalent to each of filter units 17, 43 of ultraviolet irradiators 11, 41 of the ultraviolet irradiating apparatus according to the above embodiments. Instrument 2 for ultraviolet irradiation is capable of passing ultraviolet radiation from another light source device through light-shielding filters 18 and opening 31 to form spots S, with different levels of ultraviolet radiation intensity, on the skin of the patient.

Since instrument 2 for ultraviolet irradiation can optically form spots S with different levels of ultraviolet radiation intensity through light-shielding filters 18 and opening 31, it does not need a mechanical exposure unit, is highly simple in structure, and is small in size and low in profile.

While certain preferred embodiments of the present invention have been described in detail, it should be understood that various changes and modifications may be made without departing from the spirit or scope of the appended claims.

What is claimed is:

1. An ultraviolet irradiating apparatus comprising:
   a light source for irradiating the skin of a patient with ultraviolet radiation; and
   a plurality of light-shielding filters each having different transmittances for ultraviolet radiation emitted from said light source;
   wherein said plurality of light-shielding filters are adapted to be arranged so that ultraviolet radiation can be irradiated to a plurality of spots at the same time through said plurality of light-shielding filters, whereby each of said spots receives a different intensity level of ultraviolet radiation.

2. The ultraviolet irradiating apparatus according to claim 1, further comprising:
   a land disposed closely about said light-shielding filters and projecting along an optical axis of ultraviolet irradiation from an area surrounding said light-shielding filters.

3. The ultraviolet irradiating apparatus according to claim 1, wherein said light source is of a flat structure having a pair of panels each having an ultraviolet-emission fluorescent layer.

4. The ultraviolet irradiating apparatus according to claim 3, further comprising:
   a sealing frame; and
   an ultraviolet fluorescent lamp wherein the sealing frame is interposed between the pair of panels and jointly define a hermetically sealed discharge chamber.

5. The ultraviolet irradiating apparatus according to claim 1, further comprising:
- a support member for supporting said light-shielding filters; and
- a mount, said support member being removably mounted on said mount.

6. The ultraviolet irradiating apparatus according to claim 1, further comprising:
- shutter means having a shutter unit movable between a closed position in which said shutter unit blocks the ultraviolet radiation from said light source and an open position in which said shutter unit allows the ultraviolet radiation from said light source to be applied.

7. The ultraviolet irradiating apparatus according to claim 6, wherein said shutter means has actuating means for selectively opening and closing said shutter unit.

8. The ultraviolet irradiating apparatus according to claim 1, further comprising:
- a cover for blocking ultraviolet radiation that has passed through at least one of said light-shielding filters.

9. The ultraviolet irradiating apparatus according to claim 1, further comprising:
- a cooling mechanism for cooling the light source.

10. The ultraviolet irradiating apparatus according to claim 1, further comprising:
- a controller for controlling an operation of the ultraviolet irradiating apparatus.

11. The ultraviolet irradiating apparatus according to claim 1, wherein the different transmittances of the plurality of light shielding filters range from 10% to 90%.

12. An instrument for ultraviolet irradiation, comprising:
- a plurality of light-shielding filters each having different transmittances for ultraviolet radiation emitted from a light source for irradiating the skin of a patient with ultraviolet radiation; and
- a support member for supporting said light-shielding filters;
- wherein said light-shielding filters are adapted to be arranged so that the ultraviolet radiation can be irradiated to a plurality of spots at the same time through said plurality of light-shielding filters, whereby each of said plurality of spots receives a different intensity level of ultraviolet radiation.

13. The instrument for ultraviolet irradiation according to claim 12, further comprising:
- a land disposed close to said light-shielding filters and projecting along an optical axis of ultraviolet irradiation from an area surrounding said light-shielding filters.

14. The instrument for ultraviolet irradiation according to claim 1, further comprising:
- a cover for blocking ultraviolet radiation that has passed through at least one of said light-shielding filters.

15. The instrument for ultraviolet irradiation according to claim 12, further comprising:
- a cooling mechanism for cooling the light source.

16. The instrument for ultraviolet irradiation according to claim 12, further comprising:
- a controller for controlling an operation of the instrument for ultraviolet irradiation.

17. The instrument for ultraviolet irradiation according to claim 12, wherein the different transmittances of the plurality of light shielding filters range from 10% to 90%.

* * * * *